(12) United States Patent
Poulsen

(10) Patent No.: US 10,806,866 B2
(45) Date of Patent: Oct. 20, 2020

(54) PRESSURE BASED EVENT DETECTION

(71) Applicant: Novo Nordisk A/S, Bagsvaerd (DK)

(72) Inventor: Ulrik Detlef Raedisch Poulsen, Hilleroed (DK)

(73) Assignee: Novo Nordisk A/S, Bagsvaerd (DK)

(*) Notice: Subject to any disclaimer, the term of this patent is extended or adjusted under 35 U.S.C. 154(b) by 188 days.

(21) Appl. No.: 15/737,711

(22) PCT Filed: Jul. 1, 2016

(86) PCT No.: PCT/EP2016/065544
§ 371 (c)(1),
(2) Date: Dec. 18, 2017

(87) PCT Pub. No.: WO2017/009072
PCT Pub. Date: Jan. 19, 2017

(65) Prior Publication Data
US 2018/0193569 A1 Jul. 12, 2018

(30) Foreign Application Priority Data

Jul. 10, 2015 (EP) .................. 15176265

(51) Int. Cl.
*A61M 5/32* (2006.01)
*A61M 5/20* (2006.01)
*A61M 5/315* (2006.01)
*A61M 5/24* (2006.01)

(52) U.S. Cl.
CPC ............ *A61M 5/3202* (2013.01); *A61M 5/20* (2013.01); *A61M 5/31548* (2013.01); *A61M 5/24* (2013.01);
(Continued)

(58) Field of Classification Search
CPC .. A61M 5/3202; A61M 5/31548; A61M 5/20; A61M 2205/50; A61M 5/24;
(Continued)

(56) References Cited

U.S. PATENT DOCUMENTS

| | | | |
|---|---|---|---|
| 4,565,543 A | 1/1986 | Bekkering et al. | |
| 4,844,642 A | 7/1989 | Inaba et al. | |

(Continued)

FOREIGN PATENT DOCUMENTS

| | | |
|---|---|---|
| CN | 203075363 U | 7/2013 |
| CN | 103458945 A | 12/2013 |

(Continued)

OTHER PUBLICATIONS

Bang & Olufsen Medicom a/s, C-Cap, 2006. https://web.archive.org/web/20060321041402/http:/www.medicom.bang-olufsen.com/sw706.asp?usepf=true.

(Continued)

*Primary Examiner* — Amer R Stiles
(74) *Attorney, Agent, or Firm* — Wesley Nicolas

(57) ABSTRACT

The present invention provides a drug delivery device (1) comprising a drug delivery unit (10) comprising a dose expelling mechanism operable to expel a dose of drug from a drug reservoir (11), a cap (20) configured for dismountable mounting over a portion of the drug delivery unit (10), the cap (20) comprising a cavity (25, 26) for reception of the portion of the drug delivery unit (10), a seal (40) adapted to provide a sealing in an interface between the cap (20) and the drug delivery unit (10), a sensor system (30) configured to monitor internal pressure in the cavity (25, 26) and to register an event in response to sensing a change in the internal pressure which numerically exceeds a specified threshold level over a period of less than 5 seconds, and energy means (50) for powering the sensor system (30).

10 Claims, 2 Drawing Sheets

(52) U.S. Cl.
CPC . *A61M 2205/3331* (2013.01); *A61M 2205/50* (2013.01)

(58) Field of Classification Search
CPC ............ A61M 2205/3331; A61M 5/00; A61M 5/178; A61M 5/50; A61M 5/5086; A61M 2005/3117
See application file for complete search history.

(56) References Cited

U.S. PATENT DOCUMENTS

| | | |
|---|---|---|
| 7,239,306 B2 | 7/2007 | Fahraeus et al. |
| 9,289,559 B2 | 3/2016 | Pedersen et al. |
| 9,855,395 B2 | 1/2018 | Jaffe et al. |
| 10,092,697 B2 | 10/2018 | Nessel et al. |
| 2013/0012871 A1 | 1/2013 | Pommereu |

FOREIGN PATENT DOCUMENTS

| | | |
|---|---|---|
| CN | 103827651 A | 5/2014 |
| CN | 104755118 A | 7/2015 |
| GB | 2477046 A | 7/2011 |
| JP | 2007/209675 A | 8/2007 |
| JP | 2012506279 A | 3/2012 |
| JP | 2013544154 A | 12/2013 |
| WO | 02/056822 | 7/2002 |
| WO | 2010037828 A1 | 4/2010 |
| WO | 2010046728 | 4/2010 |
| WO | WO-2010037828 A1 * | 4/2010 ........ A61M 5/31533 |
| WO | 2011124711 A1 | 10/2011 |
| WO | 2012/001493 A2 | 1/2012 |
| WO | 2012068432 | 5/2012 |
| WO | 2013034716 A1 | 3/2013 |
| WO | 2013120778 A1 | 8/2013 |
| WO | 2013/156510 A1 | 10/2013 |

OTHER PUBLICATIONS

Notey. "Intelligent Compliance C-Cap Pen Cap Helps Diabetics Take Medication." http://www.notey.com/external/3125595/intelligent-compliance-c_cap-pen-cap-helps-diabetics-take-medication-medical-bang_and_olufsen-other-stuff.html Created Oct. 23, 2007. Accessed Feb. 4, 2016. RM.

* cited by examiner

PRESSURE BASED EVENT DETECTION

CROSS-REFERENCE TO RELATED APPLICATIONS

This application is a 35 U.S.C. § 371 National Stage application of International Application PCT/EP2016/065544 (published as WO 2017/009072), filed Jul. 1, 2016, which claims priority to European Patent Application 15176265.5, filed Jul. 10, 2015; the contents of which are incorporated herein by reference.

FIELD OF THE INVENTION

The present invention relates generally to drug delivery devices, and more specifically to such devices comprising a removable protective cap.

BACKGROUND OF THE INVENTION

Lack of substantial patient compliance with established dosage intervals has long been recognised as a major problem in treating illness. Typically, a physician will recommend a patient to take a needed drug according to a specified schedule, but the actual administration of the medicine is often left to the sole control of the patient. Even a well-meaning and conscientious patient may frequently fail to take the medication at a desired time, and this may be the case even if the patient carries about the medication during the day.

Potential ill effects of such lack of compliance may be further compounded if the patient attempts to compensate for missed dosages by taking a larger dose at a later point in time. Improper dosage may for example occur when the patient cannot precisely recall taking the medication and thus is unable to correctly judge how much time has elapsed since the last dose was absorbed.

People with diseases that require regular and systematic self-managed treatment regimes, such as e.g. diabetes, are constantly facing the challenge of remembering when to take their medicine. Since such regimes can prescribe daily to weekly medication which furthermore has to be personalised to accommodate the routines of the individual, e.g. meal times, working hours, training sessions, etc. patients often need to develop their own system to help them remember the scheduled dose administrations. However, especially for people who take medicine on a regular basis the act of dose administration itself may become so ingrained that they perform e.g. injections unconsciously and then later become unsure of whether they have actually received a particular dose. This may potentially lead to dangerous double dosing incidents where the person ends up taking twice the recommended or calculated dose within a short time span.

As substantial non-compliance with a desired medication regimen is a major concern the above challenges have been addressed by a number of compliance aid devices which are adapted to provide an alarm or a reminder in case a person does not comply with a programmed schedule for taking a given dose of medicine.

For example, in WO 02/056822 (Juselius) a control device is arranged on a protective cap for an injection pen and adapted to contactlessly sense the removal of the cap from the injection pen, either capacitively or by radio field detection. This event is recognised as a dose administration and used to warn the user against double dosing within a predetermined precautionary time.

In WO 2011/124711 (Novo Nordisk A/S) a presence of an injection pen in a cavity of a protective cap is sensed by an established physical contact between an elastically supported and biased actuation member, being moved by the injection pen, and a switch in the cap. The acts of removing the pen from and subsequently repositioning the pen in the cap cavity are registered by electronic means in the cap and used to program the cap to provide a reminder to the user on when to administer a dose of the drug.

In WO 2012/001493 (Patients Pending Ltd) an electro-mechanical switch in a cap is actuated when the cap is fully mounted onto a dosing device and released when the cap is removed from the dosing device. Either the actuation or the release of the switch causes a timer to reset, after a predetermined period of time, and a display to start displaying the time elapsed since the timer was last reset, thereby indicating to the user the time elapsed since the last use of the dosing device.

Common to these prior art solutions is that they are all based on the detection of a physical presence and/or absence of a drug delivery device in a cap. This requires a precise positioning of the drug delivery device and the cap relative to one another during attachment. If, for example, the user is in a hurry and fails to arrange the two entities in the exact relative position after a dose administration the related feature offered by the particular device will be compromised and the device rendered unreliable.

Furthermore, the arrangement of the control device as an exterior attachment to the cap in WO 02/056822, as well as the radially moving switch mechanism in WO 2012/001493, tends to lead to rather bulky caps, which are generally undesired by people who need to carry their drug delivery device around during the day.

SUMMARY OF THE INVENTION

It is an object of the invention to eliminate or reduce at least one drawback of the prior art, or to provide a useful alternative to prior art solutions.

In particular, it is an object of the invention to provide a drug delivery device capable of registering the occurrence of one or more particular events related to an administration of drug therefrom.

It is a further object of the invention to provide such a device which is simple to use and which is relatively inexpensive to produce.

It is an even further object of the invention to provide such a device which can be realised in a slender configuration that is particularly attractive for users carrying it around during the day.

It is an even further object of the invention to provide such a device where the registration feature is functional even if a user does not place one part of the device in one particular position relative to another part of the device.

In the disclosure of the present invention, aspects and embodiments will be described which will address one or more of the above objects and/or which will address objects apparent from the following text.

In one aspect the invention provides a drug delivery device according to claim 1.

Thus, a drug delivery device, such as e.g. a pen injection device, may be provided which comprises a drug delivery unit comprising a dose expelling mechanism operable to expel a dose of drug from a drug reservoir, and a cap configured for dismountable mounting over a portion of the drug delivery unit. The cap may comprise a cap wall extending between a closed first end and an open second end, and defining a cavity for reception of the portion of the drug delivery unit. The drug delivery device may further comprise a seal adapted to provide a sealing in an interface between the cap and the drug delivery unit, and a powered sensor system configured to monitor internal pressure in the cavity (i.e. the local pressure in the cavity) and to register an event in response to sensing an internal pressure change in the cavity which numerically exceeds a specified threshold level and which occurs in less than 5 seconds.

The seal may be adapted to provide a gas tight, or at least substantially gas tight, sealing between the cap and the drug delivery unit when the cap is mounted on the drug delivery unit. It is noted, that the sealing need not be completely gas tight, as long as it is sufficiently tight to create a pressure change in the cavity, when the cap is being dismounted from and/or mounted onto the drug delivery unit.

The specified threshold level is set in order to avoid false positive registrations occurring due to pressure fluctuations in the surrounding space.

The basic notion is that during dismounting of the cap from the drug delivery unit a rapid pressure decrease in the cavity occurs, and during mounting of the cap onto the drug delivery unit a rapid pressure increase in the cavity occurs, both enabled by sealing means in the interface between the cap and the drug delivery unit. Such rapid pressure changes are detected by a sensor device and registered by a processor as an event. A registration of an event may comprise an assignment of a timestamp.

The cap may comprise first retention means, e.g. in the form of protrusions distributed circumferentially along an inner surface of the cap wall, and the portion of the drug delivery unit may comprise mating second retention means, e.g. in the form of a circumferential ridge, adapted to interact with the first retention means in a snap interface. The thus provided snap-fit connection between the cap and the drug delivery unit ensures that the cap, under normal operation thereof, experiences a jerk at some point during its mounting onto, and/or dismounting from, the drug delivery unit, whereby a sufficiently rapid internal pressure change in the cavity is guaranteed to occur.

Drug delivery devices of the above identified type normally undergo a cycle of cap dismounting and cap remounting in connection with an administration of drug from the drug delivery unit. A cap dismounting action may thus be viewed as an indicator of an imminent dose administration and is therefore suitable as a basis for instituting various consequential actions.

Hence, the event registration may trigger one or more dose delivery related actions. For example, the time at which the event occurs may be used as an approximate execution time for a drug administration. This time may e.g. be stored in a memory in the drug delivery device or passed on to an external recording device. Timestamps of one or more registered events may thus be used to provide an electronic log reflecting the drug administration history of the particular user.

In a very simple form the registration of an event may cause an activation of electronics in the drug delivery device, e.g. in a preparation for some particular subsequent action. A timestamp may be communicated by communication means to an external electronic device such as e.g. a mobile phone or an Internet router.

The drug delivery device may additionally comprise storage means adapted to store information relating to a use thereof, such as e.g. information relating to a registered event or information relating to a treatment regimen of the individual user, and/or an output device, e.g. in the form of an electronic display, an LED, or a loudspeaker, for conveying information relating to the use of the device, in particular to a registered event. This enables an establishment of a reminder function for alerting the user on specific details pertaining to the use of the device and/or the treatment regimen, and/or of an alarm function, e.g. for preventing double dosing. It also enables collection of information which may be used to assess e.g. adherence to a prescribed dosing interval.

The sensor device may be a barometric sensor detecting the pressure gradient directly, a switch being actuatable by the pressure gradient, or a bi-stable element being actuatable by the pressure gradient. Regardless of which, the registration is performed contactlessly and is independent of the drug delivery unit being in one specific position relative to the cap.

The seal in the interface between the drug delivery unit and the cap may comprise a flexible tight-fitting structure, e.g. a sealing ring, arranged along an outer surface of the drug delivery unit, such as around a reservoir holder, and/or arranged along an inner surface of the cap, such as along an interior portion of the cap wall. The seal is adapted to at least substantially prevent air from entering the cavity between the cap wall and the drug delivery device, and therefore it contributes significantly to the generation of a steep, fleeting pressure gradient when the cap is dismounted from, or mounted onto, the drug delivery unit in conventional manner, i.e. in less than 5 seconds, for example in less than 4 seconds, in less than 3 seconds, in less than 2 seconds, in less than 1 second, or in less than half a second. Such a pressure gradient occurs over much shorter time than natural pressure changes experienced during e.g. plane ascension, car driving, or mountain climbing, and thus presents a credible indication of a cap mounting or dismounting action. The sealing ring may be a separate component mounted along an inner circumference of the cap, or along an outer circumference of the drug delivery unit, or it may be integrated into the cap, or onto the drug delivery unit, such as by 2 K moulding.

In particular embodiments of the invention the sealing ring is arranged such that when the cap is fully mounted on the drug delivery unit an at least substantially gas tight seal is provided between the cap and a distal portion of a cartridge holder of the drug delivery unit, proximally of a needle mount portion of the cartridge holder. Thereby, the sealed internal volume of the cap is minimised, which increases the pressure changes relatively, enabling an easier detection thereof.

The sensor system may be arranged on the drug delivery unit or in the cavity, e.g. along an interior wall portion of the cap wall. In particular embodiments of the invention the cavity comprises a first cavity portion adapted to receive the portion of the drug delivery unit, and a second cavity portion adapted to accommodate the sensor system. The first cavity portion and the second cavity portion are physically separated to minimise the risk of the sensor system being damaged due to objects entering the first cavity portion. However, the first cavity portion and the second cavity portion are fluidly connected to allow the sensor system to monitor ambient pressure in the cavity as a whole.

Many users of drug delivery devices of the above discussed type store their device between uses and only removes the cap from the drug delivery unit when they are about to administer a dose. However, some users may be less stringent. Some may even play around with the device, including repeatedly dismounting and re-mounting the cap from/onto the drug delivery unit. In such cases it may be inaccurate to base the event registration on a single action.

Hence, in another aspect of the invention a drug delivery device is provided comprising A) a drug delivery unit comprising a dose expelling mechanism operable to expel a dose of drug from a drug reservoir, B) a cap configured for dismountable mounting over a portion of the drug delivery unit, the cap comprising a cavity for reception of the portion of the drug delivery unit, C) a seal adapted to provide a gas tight sealing in an interface between the cap and the drug delivery unit, and D) a sensor system configured to d1) monitor ambient pressure in the cavity, d2) detect a first event in response to sensing a decrease in the ambient pressure which numerically exceeds a first specified threshold level over a period of less than 5 seconds, d3) detect a second event in response to sensing an increase in the ambient pressure which exceeds a second specified threshold level over a period of less than 5 seconds, d4) determine a time elapsed between the first event and the second event, and d5) register a dose administration event if the time elapsed between the first event and the second event exceeds a predetermined period.

The predetermined period may be chosen in order to minimise the risk of registering false positives potentially arising from users more or less consciously manipulating the cap. In case the drug delivery device is an injection device as known from the diabetes care segment a proper use of the device will normally include the steps of cap dismounting, needle attachment, dose setting, needle insertion, dose expelling, needle retraction (and potentially removal), and cap re-mounting. Even the most experienced users need a certain amount of time to perform these steps. Hence, as one example, the predetermined period may be set to 10 seconds.

In this case the drug delivery device only registers an event as dose delivery related if the time between a cap dismounting action and a cap re-mounting action exceeds the predetermined period. An approximate execution time for a drug administration may be any time within the time range defined by the time at which the first event is detected and the second event is detected, including the terminal points. As an example, the approximate execution time for the registered dose administration event may be chosen as the time of occurrence of the second event.

In exemplary embodiments of the invention the first specified threshold level equals the second specified threshold level.

The drug delivery device may be configured to, in response to the sensor system registering a dose administration event and on the basis of a stored treatment schedule, determine a future time for a next dose administration, set a reminder for the next dose administration, and output the reminder at the future time. Thereby, the drug delivery device may offer an automatic alarm function which can be used to alert the subject user of an impending dose administration. Alternatively, or additionally, the drug delivery device may be configured to, on the basis of the determined future time for a next dose administration, provide dose related notifications to the user, such as e.g. displays of information of when the next dose administration is due etc. It is noted that, in the present context, the determined future time for a next dose administration is not necessarily an exact time of day, but may rather be a time period within which the user is recommended to administer the next dose. Hence, the reminder of the next dose administration may e.g. be output at the beginning of this time period and may contain a notification related to the time period, such as the expiry thereof.

The above sketched drug delivery devices according to the present invention possess a number of advantages over the prior art solutions. For example, 1) the sensor device and the associated electronics can be placed independently in the cap and/or in the drug delivery unit, providing for great flexibility in the design of the drug delivery device, 2) the pressure detection system itself occupies very little space, and may therefore be placed so as to cause minimal impact on the size of the drug delivery device, such as in the cavity of the cap at the end wall. Hence, the only potential contributor to an increase in the radial dimension would be the seal between the cap and the drug delivery unit, 3) the pressure detection solution does not require a physical contact between electrical components and thus has no or only minimal influence on the geometries of the drug delivery unit and the cap as well as on whether an injection needle may be mounted on the drug delivery unit when the cap is attached, providing for a flexible device configuration, 4) the pressure detection system and the seal may be implemented solely in the cap, allowing the cap to be re-used with multiple drug delivery units, including drug delivery units with different medications, and 5) in case the drug delivery unit comprises a mounted injection needle when inserted in the cap the seal will reduce the drug evaporation and thereby the risk of needle clotting.

The sensor system may be powered by energy means such as e.g. a small battery or a solar cell arrangement. The energy means may e.g. be positioned in the cavity of the cap and/or on the drug delivery unit.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein.

In the figures like structures are mainly identified by like reference numerals.

DESCRIPTION OF EXEMPLARY EMBODIMENTS

When in the following relative expressions, such as "upper" and "lower", are used, these refer to the appended figures and not necessarily to an actual situation of use. The shown figures are schematic representations for which reason the configuration of the different structures as well as their relative dimensions are intended to serve illustrative purposes only.

Figure 1:
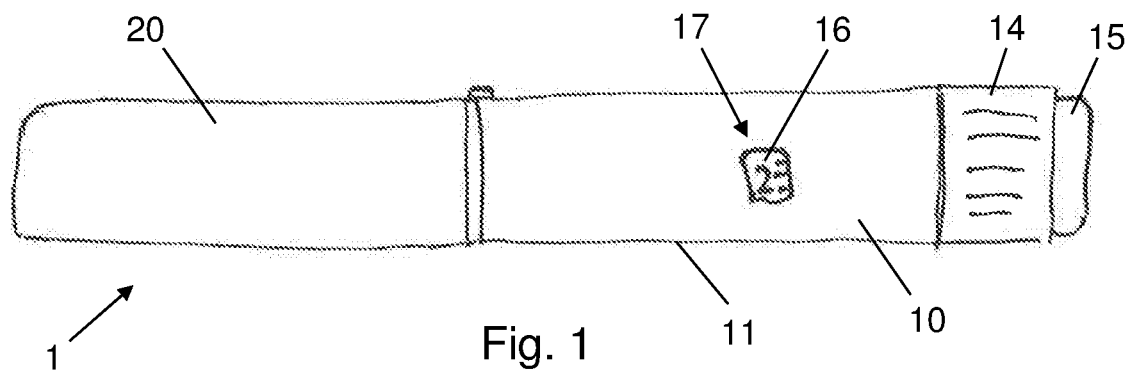
FIG. 1 is a side view of a drug delivery device according to an embodiment of the invention.

FIG. 1 is a side view of an injection device 1 according to an exemplary embodiment of the invention. The injection device 1 comprises an injection pen 10 and a protective cap 20. The injection pen 10 is of the type commonly used in the treatment of diabetes mellitus and has a tubular housing 11 provided with a proximal dose setting sleeve 14 for selective setting of a dose to be delivered, and a window 17 for display of the set dose 16. The injection pen 10 further has an injection button 15 for activation of a dose delivery mechanism accommodated in the housing 11. The cap 20 is mounted on the injection pen 10 in a manner known from the aforementioned type of injection pens.

Figure 2:
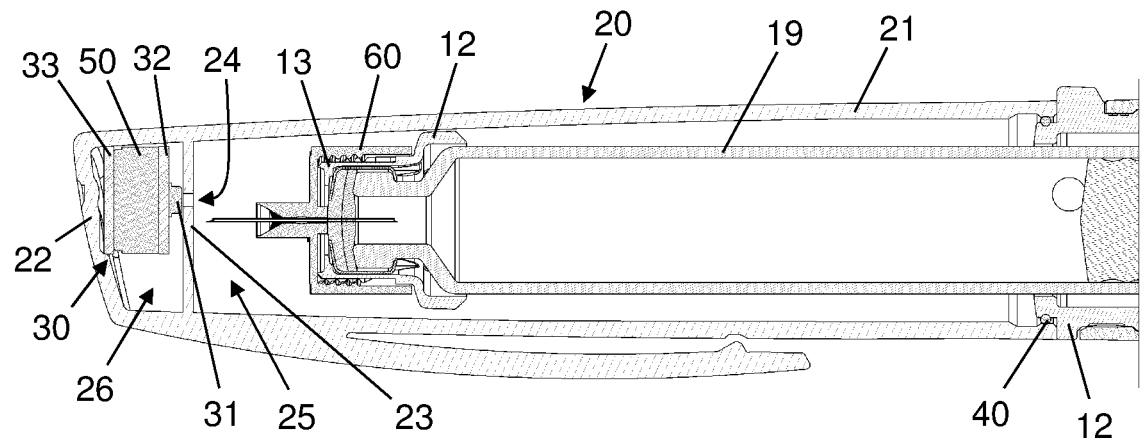
FIG. 2 is a longitudinal section view of a distal portion of the drug delivery device of FIG. 1.

FIG. 2 is a longitudinal section view of a distal portion of the injection device 1, showing the interior of the cap 20 when fully mounted on the injection pen 10. The cap 20 is defined by a substantially tubular side wall 21 and a transversal end wall 22. A transversal partition 23 with an internal vent 24 divides the interior of the cap 20 into two physically separated cavities, a proximal cavity 25 for reception of a cartridge holder 12, and a distal cavity 26 for housing a sensor system 30.

The cartridge holder 12 forms part of the injection pen 10 and serves to hold a drug cartridge 19. At its distal end the cartridge holder 12 is provided with a needle mount 13 for reception of a pen needle assembly 60. As the cap 20 is fully mounted on the injection pen 10 the cartridge holder 12 has reached the maximum entry point in the cavity 25.

The distal cavity 26 is in fluid communication with the proximal cavity 25 via the internal vent 24 and a pressure change in the proximal cavity 25 due to an insertion or retraction of the cartridge holder 12 will thus also be noticeable in the distal cavity 26. The sensor system 30 is arranged in the distal cavity 26 and comprises a barometric sensor 31 electrically connected with a combined processor and memory unit 32 and with an RF transmitter 33 adapted to automatically transmit data to an external device such as e.g. a mobile phone (not shown). The sensor system 30 is powered by a battery 50.

Exemplary pressure sensors suitable for implementation in the injection device 1 are the BMP280 from Bosch Sensortech, the MS5561C from StrainSense, or the HP203B from Rhopoint Components.

Figure 3:
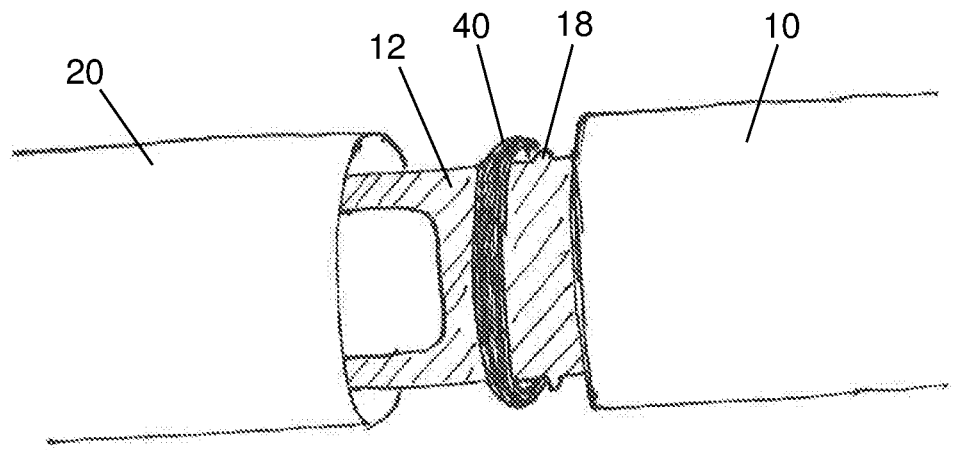
FIG. 3 is a perspective view of the drug delivery device in a cap dismounted state.

FIG. 3 is a perspective view of the injection device 1 in a state where the cap 20 is dismounted from the injection pen 10 to reveal a sealing ring 40 arranged tightly around the cartridge holder 12 just distally of a circumferential ridge 18 which serves as a snap fit between the cap 20 and the injection pen 10. The sealing ring 40 is elastomeric and provides a gas tight, or substantially gas tight, sealing between the cartridge holder 12 and the side wall 21, when the cap 20 is fully mounted on the injection pen 10. It is noted that the sealing ring 40 could alternatively be positioned at a more distal portion of the cartridge holder 12, or along an inner portion of the side wall 21.

A rubber Y-seal ring is particularly suitable for use as sealing in the injection device 1. However, other seals may alternatively be used, such as e.g. a conventional O-ring. Sufficient sealing can also be obtained by having a press fit geometry between the cap and the drug delivery unit.

EXAMPLE

Figure 4:
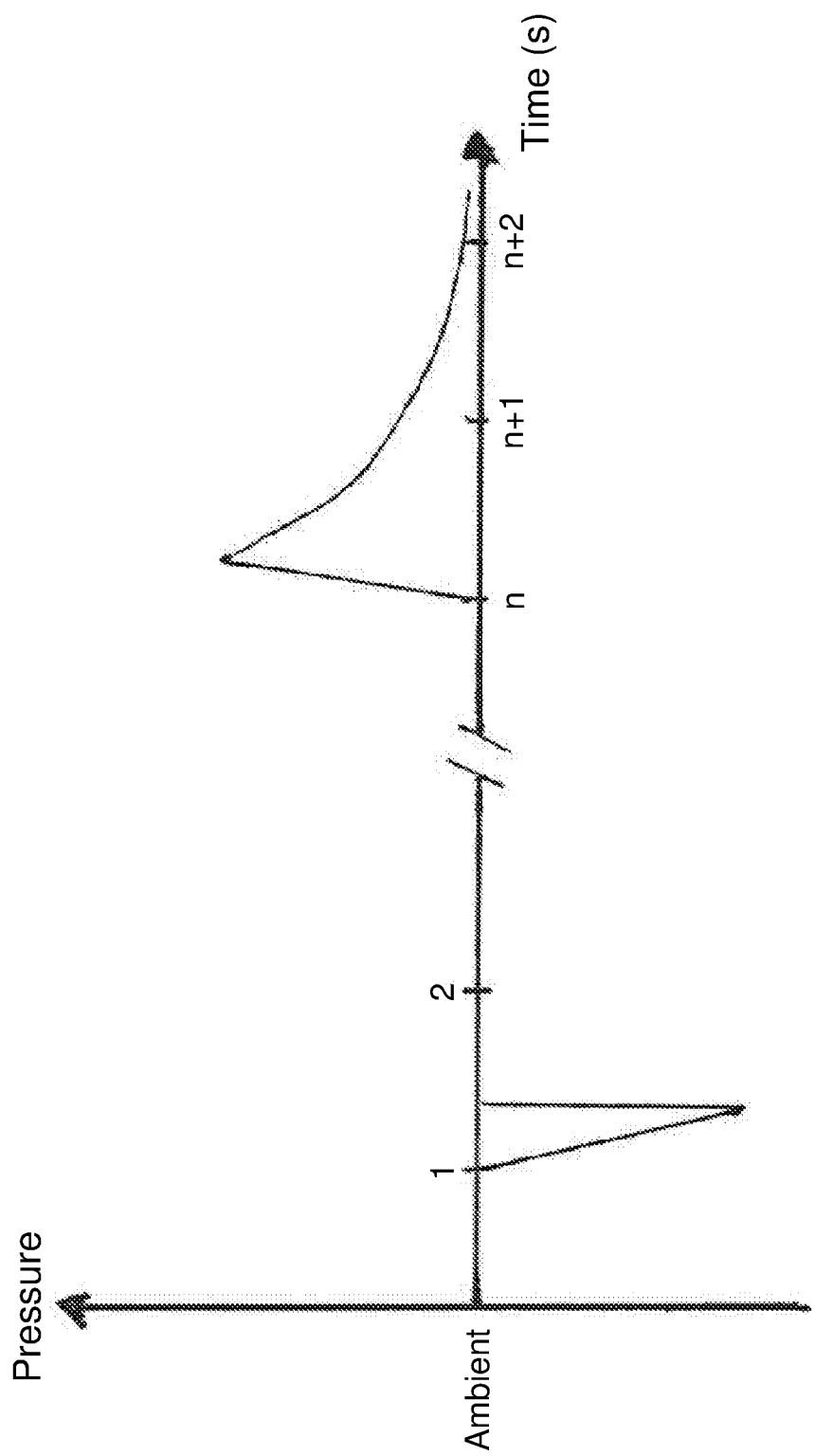
FIG. 4 is a graph illustrating dosing related events registered by the drug delivery device.

FIG. 4 is a graph which qualitatively illustrates the event logging functionality of the injection device 1. At time t=1 second a user pulls off the cap 20 from the injection pen 10. The action takes less than half a second and causes a fleeting local pressure drop of 20 mbar in both the proximal cavity 25 and the distal cavity 26 as the sealing ring 40 slides along the side wall 21. This pressure drop is detected by the sensor system 30, and since it fulfils both requirements of numerically exceeding the specified threshold level and taking less than 5 seconds it is registered as a cap off event. Subsequently, at time t=n seconds, the user puts the cap 20 back onto the injection pen 10. This action causes a fleeting local pressure rise of 80 mbar in both the proximal cavity 25 and the distal cavity 26 and is detected by the sensor system 30. Since the pressure rise fulfils both requirements of numerically exceeding the specified threshold level and taking less than 5 seconds it is registered as a cap on event. In this example the sensor system 30 detected numerical pressure changes in the range 20-80 mbar. It is noted, that the experienced pressure changes are dependent on the sealed internal cap volume as well as on the air tightness of the sealing between the cap and the injection pen and the rate of cap mounting/dismounting.

The injection device 1 has now registered a cap off event at t=1 second and a cap on event at t=n seconds. If n−1≤a predetermined period (of e.g. 10 seconds) the two events will be ignored as noise signals. However, if n−1>the predetermined period the injection device 1 will log a dose administration event and automatically transmit information thereof, including a timestamp, to a predefined mobile phone entity via the RF transmitter 33.

The mobile phone receives the information and generates a reminder for a next dose administration based on the information from the injection device 1 as well as a pre-programmed administration schedule. It is noted, that instead of, or in addition to, the RF transmitter 33 the injection device 1 may comprise an electronic display and/or a tone generator for visually displaying and/or audibly outputting a reminder generated by the processor 32.

The invention claimed is:
1. A drug delivery device comprising:
   a drug delivery unit comprising a dose expelling mechanism operable to expel a dose of drug from a drug reservoir,
   a cap configured for dismountable mounting over a portion of the drug delivery unit, the cap comprising a cavity for reception of the portion of the drug delivery unit,
   a seal adapted to provide a sealing in an interface between the cap and the drug delivery unit,
   a sensor system configured to monitor internal pressure in the cavity and to register an event in response to sensing a change in the internal pressure which numerically exceeds a specified threshold level over a period of less than 5 seconds, and
   energy means for powering the sensor system.
2. The drug delivery device according to claim 1, wherein the sensor system comprises a barometric pressure sensor.
3. The drug delivery device according to claim 1, wherein the cavity comprises a first cavity portion in which the portion of the drug delivery unit is positionable, and a second cavity portion being separated from, yet fluidly connected with, the first cavity portion, and
   wherein the sensor system is arranged in the second cavity portion.
4. The drug delivery device according to claim 1, wherein the cap comprises first retention means and the portion of the drug delivery unit comprises mating second retention means adapted to interact with the first retention means to provide a snap-fit connection.

5. The drug delivery device according to claim 1, wherein the seal comprises a sealing ring mounted along, or being integral with, an outer circumference of the drug delivery unit.

6. The drug delivery device according to claim 1, wherein the seal comprises a sealing ring mounted along, or being integral with, an inner circumference of the cap.

7. The drug delivery device according to claim 1, further comprising an output device for conveying information relating to a registered event.

8. The drug delivery device according to claim 1, further comprising storage means for storing information relating to a registered event.

9. The drug delivery device according to claim 1, wherein the sensor system is configured to:
   register a first event in response to sensing a decrease in the internal pressure which numerically exceeds a first specified threshold level over a period of less than 5 seconds,
   register a second event in response to sensing an increase in the internal pressure which exceeds a second specified threshold level over a period of less than 5 seconds,
   determine a time elapsed between the first event and the second event, and
   register a dose administration event if the time elapsed between the first event and the second event exceeds a predetermined period.

10. The drug delivery device according to claim 9, further comprising an output device and storage means, wherein the drug delivery device is configured to, on the basis of a registered dose administration event and a stored treatment schedule,
   determine a future time for a next dose administration,
   set a reminder for the next dose administration, and
   output the reminder at the future time.

* * * * *